US00PP27239P2

(12) United States Plant Patent
Klemm et al.

(10) Patent No.: US PP27,239 P2
(45) Date of Patent: Oct. 4, 2016

(54) ***PETUNIA* PLANT NAMED 'KLEPH14246'**

(50) Latin Name: *Petunia hybrida*
Varietal Denomination: KLEPH14246

(71) Applicant: Klemm+Sohn GmbH & Co. KG, Stuttgart (DE)

(72) Inventors: Nils Klemm, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 14/545,761

(22) Filed: Jun. 15, 2015

(51) Int. Cl.
*A01H 5/02* (2006.01)

(52) U.S. Cl.
USPC ..... Plt./356.2

(58) Field of Classification Search
USPC ..... Plt./356.2
CPC ..... A01H 5/02
See application file for complete search history.

*Primary Examiner* — Kent L Bell
(74) *Attorney, Agent, or Firm* — Bethany R. Roahrig; Barbara Campbell; Cochran Freund & Young, LLC

(57) ABSTRACT

A new *petunia* plant particularly distinguished by having double flowers colored light purple with purple veins and a mounding plant habit, is disclosed.

1 Drawing Sheet

Genus and species: *Petunia hybrida.*
Variety denomination: 'KLEPH14246'.

BACKGROUND OF THE NEW PLANT

The present invention comprises a new and distinct variety of *petunia*, botanically known as *Petunia hybrida*, and hereinafter referred to by the variety name 'KLEPH14246'. 'KLEPH14246' originated from a controlled-cross between the proprietary female *petunia* variety 'PH-2009-1210' (unpatented) and male proprietary *petunia* variety 'PH-2009-1189' (unpatented).

In July 2010, two *petunia* parental lines, the female variety 'PH-2009-1210' and the male *petunia* variety 'PH-2009-1189' were crossed via a controlled cross in Latina, Italy and seeds were obtained. The seeds were sown and plants were grown for evaluation. A plant line was selected in April 2011 which had double flowers colored light purple with purple veins and was subsequently named 'KLEPH14246'. In May 2011, 'KLEPH14246' was first vegetatively propagated by terminal tip cuttings and tissue culture in Latina, Italy. 'KLEPH14246' was found to reproduce true to type in successive generations of asexual propagation via tissue culture and terminal tip cuttings.

SUMMARY

The following are the most outstanding and distinguishing characteristics of this new variety when grown under normal horticultural practices in Latina, Italy.

1. Double flowers;
2. Light purple with purple vein colored flowers; and
3. A mounding plant habit.

DESCRIPTION OF THE PHOTOGRAPH

This new *petunia* plant is illustrated by the accompanying photograph which shows the flowers and foliage of the plant. The photograph is of a three-month-old plant grown in a greenhouse in Stuttgart, Germany in May 2014. The colors shown are as true as can be reasonably obtained by conventional photographic procedures.

DESCRIPTION OF THE NEW VARIETY

The following detailed descriptions set forth the distinctive characteristics of 'KLEPH14246'. The data which define these characteristics were collected from asexual reproductions carried out in Latina, Italy. Data was collected on twelve-week-old plants grown in plastic greenhouse in Latina, Italy in February 2015. Color references are to The R.H.S. Colour Chart of The Royal Horticultural Society of London (R.H.S.), 5$^{th}$ edition (2007).

Classification:
- *Family.*—Solanaceae.
- *Species.*—*Petunia hybrida.*
- *Common name.*—*Petunia.*
- *Variety.*—'KLEPH14246'.

Parentage:
- *Female.*—Proprietary female *petunia* 'PH-2009-1210' (unpatented).
- *Male.*—Proprietary male *petunia* 'PH-2009-1189' (unpatented).

Plant description:
- *Form.*—Medium vigor.
- *Habit.*—Mounding.
- *Height (from top of soil).*—About 10.0 cm.
- *Width.*—About 21.0 cm.
- *Propagation.*—Terminal tip cuttings and tissue culture.
- *Time to produce a finished flowering plant.*—About 14 weeks in winter under short day conditions; 7 weeks in spring.
- *Time to initiate and develop roots.*—2 to 3 weeks.
- *Root description.*—Moderate density, moderate branching, white roots.

Stems:
- *Average number (basal).*—About 14.

*Length of basal branches* (*from the base of the stem to the tip*).—About 11.0 cm.
*Internode length*.—0.75 cm to 1.5 cm.
*Diameter of branches* (*from midpoint*).—0.6 cm.
*Stem color*.—RHS 145B.
*Anthocyanin*.—Absent.
*Texture*.—Tomentose.

Leaves:
*Arrangement*.—Alternate.
*Length*.—4.0 cm to 9.0 cm.
*Width*.—2.5 cm to 3.5 cm.
*Shape*.—Elliptic.
*Apex*.—Acute.
*Base*.—Attenuate.
*Margin*.—Entire.
*Immature leaf color*.—Upper surface: RHS 137B. Lower surface: RHS 146C.
*Mature leaf color*.—Upper surface: RHS N137C. Lower surface: RHS 146A.
*Texture* (*both surfaces*).—Tomentose.
*Venation pattern*.—Arcuate.
*Venation color*.—Upper surface: RHS 146C. Lower surface: RHS 146D.
*Petioles*.—Length: 0.2 cm to 0.5 cm. Diameter: 0.3 cm. Color: RHS 146C. Texture: Tomentose.

Flower buds:
*Shape*.—Irregular oblong.
*Length*.—2.0 cm to 3.3 cm.
*Diameter*.—0.7 cm to 1.3 cm.
*Color at tight bud*.—RHS 1C.
*Texture*.—Slightly pubescent.

Inflorescence:
*Blooming habit* (*flowering season*).—Permanent flowering during the summertime.
*Inflorescence type*.—Cymose.
*Number of flowers per node*.—1.
*Lastingness of individual blooms on the plant*.—7 to 10 days.
*Fragrance*.—Absent.
*Flowers*.—Arrangement: Composed of 16 to 18 petals irregularly fused in a rosette. Diameter (flower face): 6.0 cm. Depth (total length of flower): 5.0 cm. Throat/Funnel: Length: 2.5 cm. Diameter (at opening): 1.3 cm. Texture (both inner and outer surfaces): Smooth, glabrous. Color: Inner surface: RHS 83A. Outer surface: RHS 84D. Petals: Color, mature flower (fully opened): Upper surface: RHS 84B with RHS N82A veins. Lower surface: RHS 76B. Apex: Slightly mucronate. Base: Fused. Margin: Entire. Strength of waviness: Strong. Degree of lobation: Weak. Calyx arrangement: Actinomorphic, composed of 5 sepals.
*Sepals*.—Color: Upper surface: RHS 137B. Lower surface: RHS 137C. Length: 1.7 cm to 2.0 cm. Width: 0.3 cm to 0.5 cm. Shape: Narrowly oblong. Apex: Acute. Base: Attenuate. Margin: Entire. Texture (both surfaces): Pubescent.
*Pedicels*.—Color: RHS 144A. Length: About 3.0 cm. Diameter: 0.2 cm. Texture: Pubescent.

Reproductive organs:
*Stamens*.—Quantity: 5 or more. Shape: Irregularly fused to the petals. Anther: Shape: Elliptic. Color: RHS 4D. Length: 0.3 cm. Diameter: 0.2 cm. Pollen: Color: RHS 188D. Amount: Sparse. Pistils: Quantity per flower: 1. Length: 0.3 cm. Stigma color: RHS 143A. Style color: RHS 145B.

Fruit/seed set: None observed.
Disease/insect resistance: None observed.

COMPARISON WITH PARENTAL LINES AND KNOWN VARIETY

'KLEPH14246' is a distinct variety of *petunia* and is distinguished from its parents as described in Table 1:

TABLE 1

Comparison with Parental Lines

| Trait | Variety 'KLEPH14246' | Female parent 'PH-2009-1210' | Male Parent 'PH-2009-1189' |
|---|---|---|---|
| Flower color | Light purple with purple veins | White | White |
| Flower shape | Double | Single | Double |

'KLEPH14246' is most similar to the commercial line *petunia* plant named 'Tumbelina Priscilla' (patent status unknown). Differences between the two varieties are described in Table 2:

TABLE 2

Comparison with Similar Variety

| Trait | Variety 'KLEPH14246' | Commercial line 'Tumbelina Priscilla' |
|---|---|---|
| Flower size | Bigger flowers than 'Tumbelina Priscilla' | Smaller flowers than 'KLEPH14246' |
| Vein color | Lighter veins | Darker veins |

We claim:

1. A new and distinct variety of *petunia* plant named 'KLEPH14246' as illustrated and described herein.

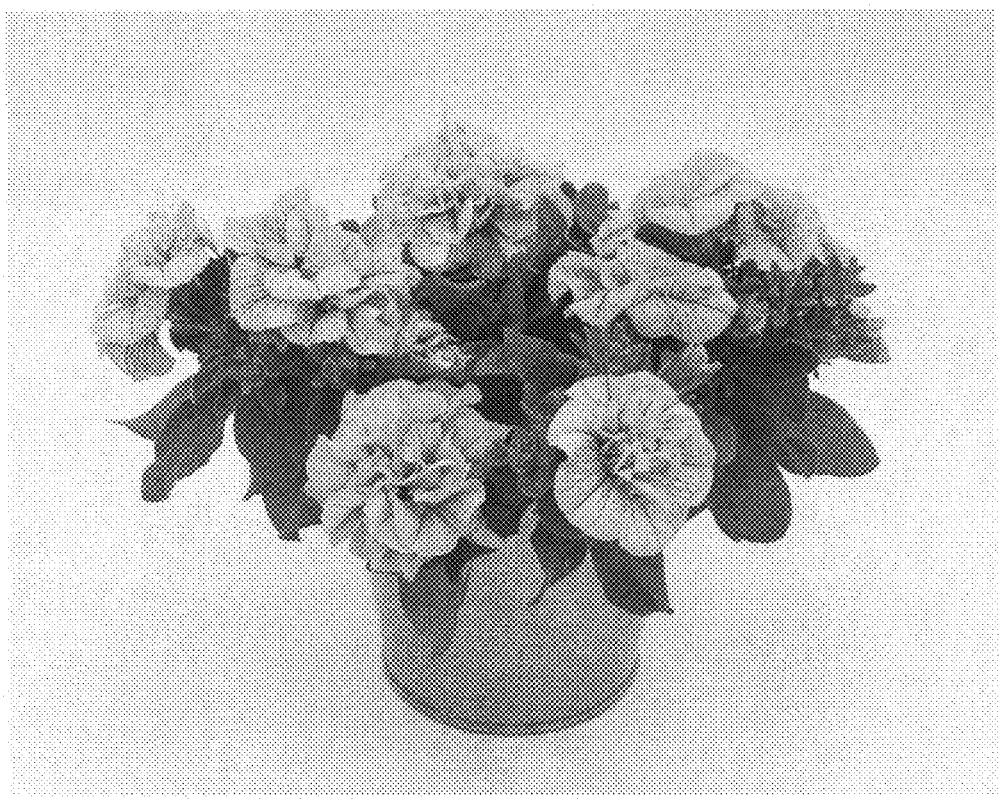

* * * * *